United States Patent
Lesmeister et al.

(10) Patent No.: US 10,363,155 B2
(45) Date of Patent: Jul. 30, 2019

(54) STENT GRAFT

(71) Applicant: JOTEC GMBH, Hechingen (DE)

(72) Inventors: Rainer Lesmeister, Wannweil (DE); Franz-Peter Barthold, Balingen (DE)

(73) Assignee: JOTEC GMBH, Hechingen (DE)

( * ) Notice: Subject to any disclaimer, the term of this patent is extended or adjusted under 35 U.S.C. 154(b) by 536 days.

(21) Appl. No.: 14/975,541

(22) Filed: Dec. 18, 2015

(65) Prior Publication Data

US 2016/0100969 A1   Apr. 14, 2016

Related U.S. Application Data

(63) Continuation of application No. PCT/EP2014/062784, filed on Jun. 18, 2014.

(30) Foreign Application Priority Data

Jun. 20, 2013   (DE) .................. 10 2013 106 463

(51) Int. Cl.
*A61F 2/97*   (2013.01)
*A61F 2/07*   (2013.01)
(Continued)

(52) U.S. Cl.
CPC .................. *A61F 2/97* (2013.01); *A61F 2/07* (2013.01); *A61F 2/844* (2013.01); *A61F 2/89* (2013.01); *A61F 2002/9511* (2013.01)

(58) Field of Classification Search
CPC .... A61F 2/97; A61F 2/07; A61F 2/844; A61F 2/89; A61F 2002/9511; A61F 2/95; A61F 2/962; A61F 2/9665
See application file for complete search history.

(56) References Cited

U.S. PATENT DOCUMENTS 5,873,906 A *  2/1999  Lau .......................... A61F 2/07
                                                    128/898
6,899,727 B2   5/2005  Armstrong et al.
(Continued)

FOREIGN PATENT DOCUMENTS

DE    103 35 948         2/2005
DE    103 46 200 A1      5/2005
(Continued)

OTHER PUBLICATIONS

International Preliminary Report on Patentability for PCT/EP2014/062784, dated Dec. 30, 2015, 13 pages (Including English translation).
(Continued)

*Primary Examiner* — David C Eastwood
(74) *Attorney, Agent, or Firm* — Rimon, P.C.

(57) ABSTRACT

A stent graft comprises a hollow cylindrical body and a sleeve catheter, wherein the body comprises at least a self-expanding stent and prosthetic material, wherein the body has a circumference in a compressed state which is smaller than a circumference of the body in an expanded state. The sleeve catheter is embodied as a flap-shaped compression element comprising two longitudinal edges, wherein a first longitudinal edge is attached to the body, wherein an extent of the flap-shaped compression element perpendicular to the first longitudinal edge is smaller than the circumference of the body in the expanded state, wherein, for compressing the body, the flap-shaped compression element can be placed around the body and a free second longitudinal edge is detachably fixable to fixation points arranged on the body and/or on the flap-shaped compression element.

12 Claims, 4 Drawing Sheets

(51) Int. Cl.
*A61F 2/89* (2013.01)
*A61F 2/844* (2013.01)
*A61F 2/95* (2013.01)

(56) References Cited

U.S. PATENT DOCUMENTS

| | | | |
|---|---|---|---|
| 9,226,839 B1* | 1/2016 | Kariniemi | A61F 2/852 |
| 9,861,503 B2* | 1/2018 | Barthold | A61F 2/82 |
| 2002/0029077 A1* | 3/2002 | Leopold | A61F 2/07 |
| | | | 623/1.11 |
| 2002/0099431 A1* | 7/2002 | Armstrong | A61F 2/95 |
| | | | 623/1.11 |
| 2006/0015171 A1* | 1/2006 | Armstrong | A61B 17/12022 |
| | | | 623/1.12 |
| 2006/0247757 A1 | 11/2006 | Kaufmann et al. | |
| 2007/0100427 A1 | 5/2007 | Perouse | |
| 2009/0082842 A1* | 3/2009 | Glynn | A61F 2/91 |
| | | | 623/1.11 |
| 2010/0152711 A1* | 6/2010 | Utke | A61F 2/95 |
| | | | 604/528 |
| 2011/0230951 A1 | 9/2011 | Cully et al. | |
| 2012/0022630 A1* | 1/2012 | Wubbeling | A61F 2/95 |
| | | | 623/1.11 |
| 2012/0046652 A1* | 2/2012 | Sokel | A61F 2/95 |
| | | | 606/1 |
| 2012/0130473 A1* | 5/2012 | Norris | A61F 2/97 |
| | | | 623/1.12 |
| 2012/0130475 A1* | 5/2012 | Shaw | A61F 2/97 |
| | | | 623/1.12 |
| 2012/0296360 A1* | 11/2012 | Norris | A61F 2/97 |
| | | | 606/191 |
| 2013/0123896 A1* | 5/2013 | Bloss | A61F 2/95 |
| | | | 623/1.11 |
| 2013/0150945 A1 | 6/2013 | Crawford et al. | |
| 2013/0158647 A1* | 6/2013 | Norris | A61F 2/97 |
| | | | 623/1.12 |
| 2013/0211498 A1* | 8/2013 | Buckley | A61F 2/954 |
| | | | 623/1.16 |
| 2013/0245742 A1* | 9/2013 | Norris | A61F 2/95 |
| | | | 623/1.11 |
| 2014/0336745 A1* | 11/2014 | Barthold | A61F 2/07 |
| | | | 623/1.12 |

FOREIGN PATENT DOCUMENTS

| | | |
|---|---|---|
| EP | 1 964 532 | 9/2008 |
| WO | WO-2011/063972 | 6/2011 |
| WO | WO 2012/068257 A2 | 5/2012 |

OTHER PUBLICATIONS

International Search Report and Written Opinion on PCT/EP2014/062784, dated Sep. 4, 2014, 15 pages (Including English translation).

* cited by examiner

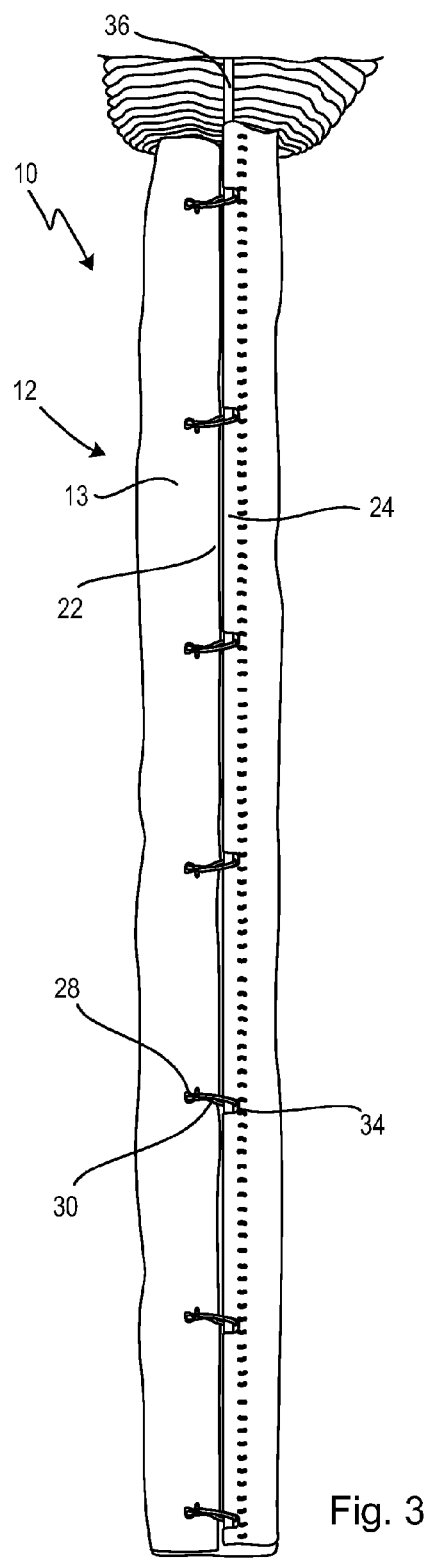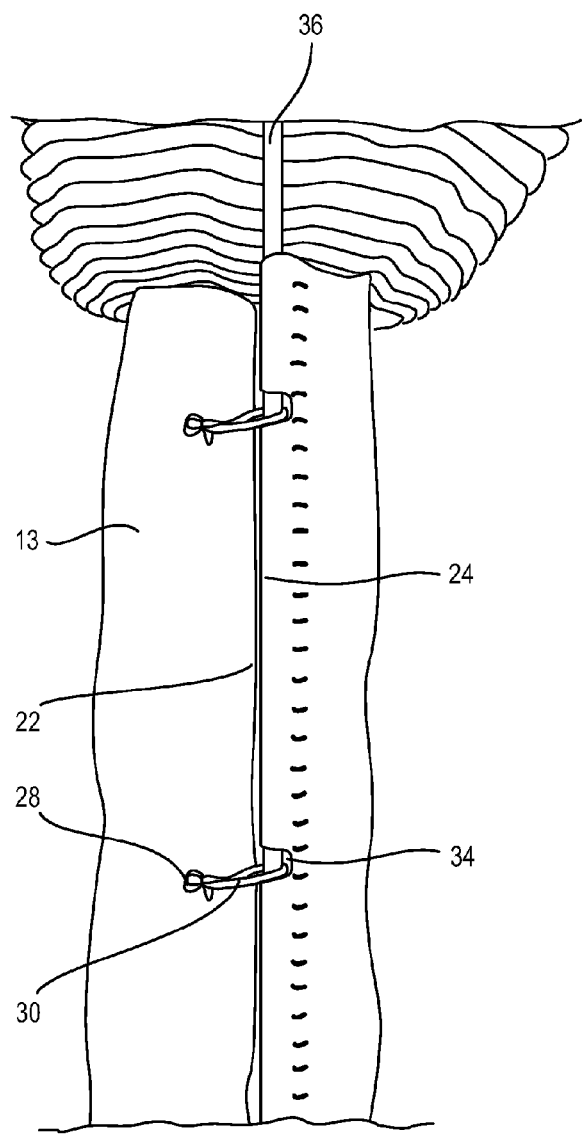
Fig. 3
Fig. 4

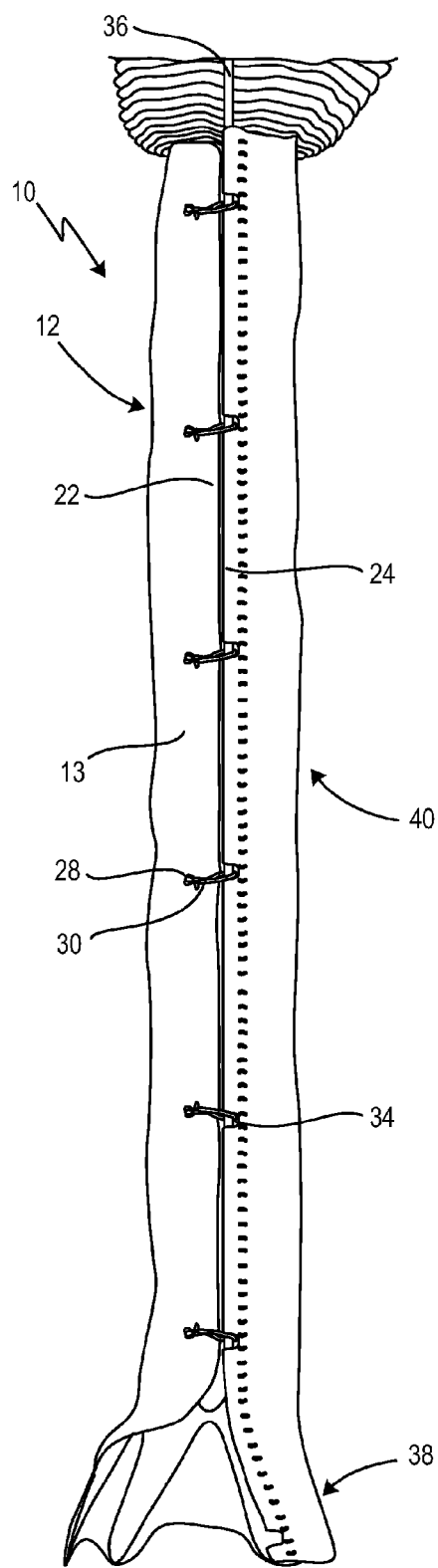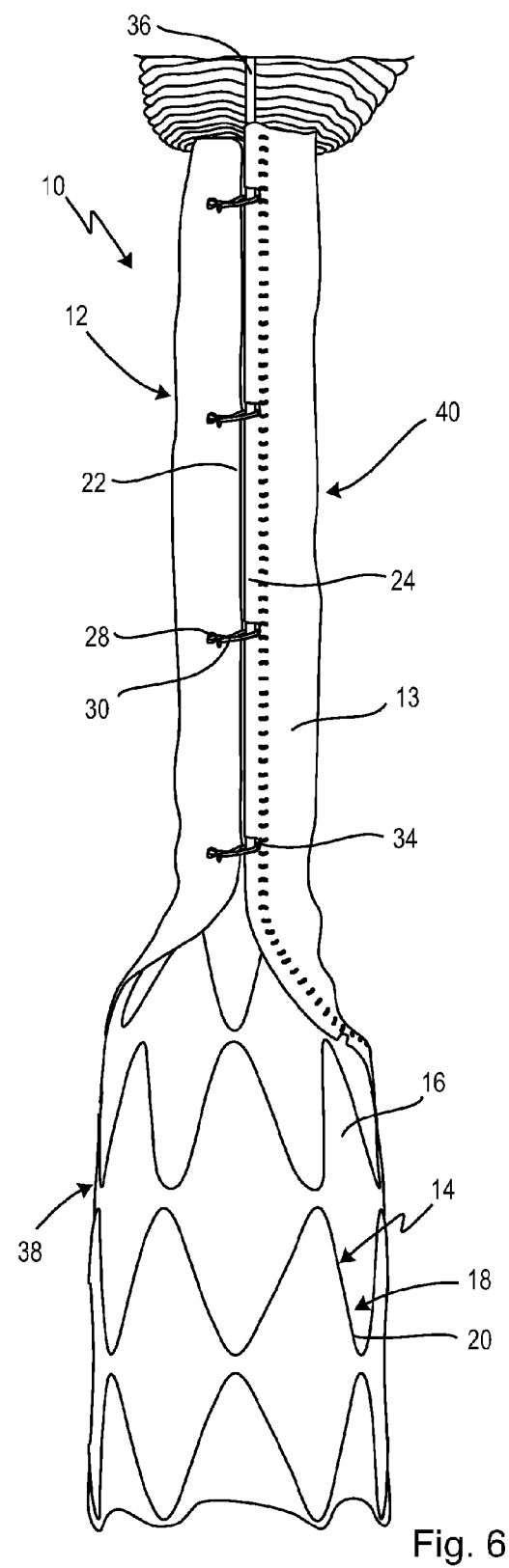

STENT GRAFT

CROSS-REFERENCES TO RELATED APPLICATIONS

This application is a continuation of international patent application PCT/EP2014/062784, filed on Jun. 18, 2014, designating the U.S., which international patent application has been published in German language and claims priority from German patent application DE 10 2013 106 463.9, filed on Jun. 20, 2013. The entire contents of these priority applications are incorporated herein by reference.

BACKGROUND OF THE INVENTION

The present invention relates to a stent graft with a hollow cylindrical body and a sleeve catheter, wherein the body has at least one self-expanding stent and a prosthetic material, wherein the body, in a compressed state, has a circumference that is smaller than a circumference of the body in an expanded state.

Stent grafts of this kind are well known in the prior art. These are in the form of a medical implant which is inserted into hollow organs, for example blood vessels, of a patient in order to keep open any constrictions that have been caused there by disease and, by so doing, to maintain the flow of blood. Moreover, stent grafts are used for the intravascular treatment of aneurysms, dissections and other specific lesions. The stent graft usually has a hollow cylindrical shape with a longitudinal extent, such that blood is able to flow through the hollow space of the stent graft in the implanted state.

However, in order to ensure that such a stent graft remains effective for the period of treatment in the blood vessel of a patient, it is necessary for the stent graft to be fixed in position at the site that is to be treated. This is permitted by a sufficiently large contact area between the jacket surface of the stent graft and the vessel wall, wherein the stent graft has to lie with its jacket surface snugly on the vessel wall.

In the prior art, therefore, stent grafts are known which have a self-expanding stent and are therefore compressible and expansible again. They can therefore adopt at least two states, namely a compressed state and an expanded state. For implantation, the stent graft is initially compressed in the radial direction such that the diameter of the hollow cylindrical body is reduced at least to the extent that the latter is insertable into the blood vessel of the patient. In order to produce the compressed state, the stent graft is introduced into a sheath designated as a sleeve catheter. The sleeve catheter for this purpose has a circumference that is smaller than the circumference of the stent graft in the expanded state. In the compressed state, the stent graft, together with the sleeve catheter enclosing it, is inserted into a blood vessel and then positioned at the pathological site, it being possible to monitor the position of the stent graft with the aid of X-ray markers. Once the desired position or orientation of the stent graft is reached, the sleeve catheter is withdrawn, as a result of which the stent graft is released and is able to expand. On account of the self-expansion property of the stent, the stent graft stretches open in the blood vessel. As a result of the pressure force between the stent graft and the vessel wall, the stent graft remains fixed in place at the desired position. The blood vessel can thus be kept open and the flow of blood maintained.

In the prior art, for example, stent grafts are known in which the stent is formed as a wire structure, which is responsible for the self-expansion property of the stent. The wire structure is normally made of metal or plastic and is moreover enclosed by a prosthetic material, which is secured on the wire structure. The prosthetic material can be composed of textile material, for example a woven polyester fabric impervious to blood. The biocompatibility of such materials means that the contact between the vessel wall and the expanded stent graft is free of complications.

DE 103 35 948 B3 discloses a stent graft with an aforementioned stent, wherein the stent in the expanded state is able to be compressed again with the aid of a thread after the stent graft has been inserted into a blood vessel of the patient. This therefore permits the removal of a stent graft that has already been inserted into a blood vessel.

WO 2011/063972 A1 and US 2007/0100427 A1 disclose a similar stent graft in which, with the aid of one or more threads, the diameter of the stent graft can be changed after it has been inserted. EP 1 964 532 A2 discloses a further stent graft in which the sleeve catheter can be pulled back in stages.

In all of the aforementioned documents, the sleeve catheter is designed as a separate sleeve tube into which the body of the stent graft is pushed and thereby compressed. However, this has the disadvantage that the compression is made difficult since the person carrying out the treatment has to fold the body of the stent graft up in portions and at the same time insert it into the sleeve catheter until the latter fully encloses the body of the stent graft. Moreover, the withdrawal of the sleeve catheter in order to expand the hollow cylindrical body of the stent graft is associated with frictional forces, on the one hand, between the sleeve catheter and the vessel wall and, on the other hand, between the sleeve catheter and the body of the stent graft. This may, on the one hand, cause damage to the vessel wall and, on the other hand, cause the stent graft to be displaced or twisted from its previously adopted optimal position. The latter scenario necessitates awkward repositioning of the stent graft in the blood vessel.

SUMMARY OF THE INVENTION

Against this background, the object of the invention is to develop a stent graft of the type mentioned at the outset in such a way that the body can be compressed in a simple way and can likewise be easily released and expanded in a blood vessel with less friction.

According to the invention, the aforementioned object is achieved by the fact that the sleeve catheter is designed as a flap-shaped compression element having two longitudinal edges, wherein a first longitudinal edge is secured on the body, wherein an extent of the flap-shaped compression element perpendicular to the first longitudinal edge is smaller than the circumference of the body in the expanded state, wherein, for the purpose of compressing the body, the flap-shaped compression element can be placed around the body and a free, second longitudinal edge is releasably attachable to fixation points arranged on the body and/or on the flap-shaped compression element.

According to the invention, the sleeve catheter is designed as a flap-shaped compression element and has two longitudinal edges, wherein a first longitudinal edge is secured on the body. Thus, in contrast to the prior art, the sleeve catheter is secured on the stent graft. Moreover, the flap-shaped compression element has an extent, perpendicular to the first longitudinal edge, that is smaller than the circumference of the body of the stent graft in the expanded state. In this way, the body of the stent graft can be compressed by means of the flap-shaped compression element prior to insertion into a blood vessel. Fixation points for securing the free longitudinal edge of the flap-shaped compression element are arranged on the body of the stent graft and/or on the flap-shaped compression element.

In order to compress the body of the stent graft, the flap-shaped compression element is placed around the body in such a way that the flap-shaped compression element partially or completely encloses the body. The stent is thus compressed radially inward and the cross section of the body of the stent graft decreases in size. The second longitudinal edge is then releasably attached to the fixation points arranged on the body and/or on the flap-shaped compression element. The body is thus able to be compressed by a wrapping movement, which permits advantageously simpler handling than the insertion of the stent graft into a sleeve tube. A further advantage is that, by virtue of the flap-shaped compression element, the stent graft, after it has been compressed, has a smooth surface that facilitates the insertion of the stent graft into a blood vessel.

After the stent graft has been inserted into a blood vessel and the stent graft has been positioned at the desired site, the second longitudinal edge can be detached from the fixation points in order to expand the body of the stent graft. However, the flap-shaped compression element is not withdrawn from the blood vessel; instead it remains on the body of the stent graft in the blood vessel. This is permitted by the fact that the compression element is secured with the first longitudinal edge to the body, such that there is no danger of the compression element migrating in the blood vessel. Since the sleeve catheter formed by the compression element is not withdrawn from the blood vessel, frictional forces between the sleeve catheter and the vessel wall and between the sleeve catheter and the body of the stent graft are avoided, as a result of which it is possible to avoid damage to the vessel wall and to avoid the repositioning that is necessary if the stent graft changes position. A further advantage of the stent graft according to the invention is that the operating time can be reduced.

In a preferred embodiment, the flap-shaped compression element, in the compressed state of the body, extends perpendicularly with respect to the first longitudinal edge and at least fully circumferentially about the body of the stent graft.

With this measure, the body can advantageously be compressed to its smallest possible external diameter. The compressed state of the body thereby achieved is also uniform about the entire circumference of the stent graft, which makes it easier to insert the stent graft into the blood vessel and to position the stent graft in the blood vessel.

In another preferred embodiment, the flap-shaped compression element has substantially the same length as the body.

With this measure, the body is able to be compressed uniformly along its entire length. This additionally facilitates the insertion of the stent graft into a blood vessel and the positioning of the stent graft in the blood vessel.

In another preferred embodiment, the first longitudinal edge of the flap-shaped compression element is secured on the prosthetic material.

This measure has the advantage that the flap-shaped compression element can be fixed particularly easily to the body of the stent graft. The flap-shaped compression element can, like the prosthetic material, have a textile structure, such that the flap-shaped compression element can easily be secured on the prosthetic material, for example by stitches. Securing with stitches has the advantage that the smoothness of the surface of the stent graft is not impaired and that the flap-shaped compression element does not separate from the body.

In another preferred embodiment, the fixation points arranged on the body and/or on the flap-shaped compression element have loops through which a rod can be threaded for securing the second longitudinal edge of the flap-shaped compression element.

With this measure, a simple method for expanding the body is advantageously made available in which no frictional force arises between the stent graft and the sleeve catheter, only between the loops and the rod, said frictional force that arises being substantially less than when pulling the sleeve catheter off from the stent graft and pulling the sleeve catheter out of the blood vessel. The rod can have a particularly smooth and therefore low-friction surface and be made, for example, of stainless steel, and it therefore does not cause damage to the vessel wall when being pulled out. Thus, the frictional force arising during the expansion of the body can be greatly reduced and the time needed for the expansion can be shortened. Moreover, when the rod is pulled out, the body is not pulled with it. Furthermore, the loops can be easily secured to the body and/or to the flap-shaped compression element, for example by tying. It will be appreciated that each fixation point can have one or more loops.

In another preferred embodiment, the second longitudinal edge of the flap-shaped compression element has a hemstitch into which the rod is insertable.

This measure is advantageous since the entire free second longitudinal edge can be secured uniformly to the body by insertion of the rod, of which the length preferably exceeds the length of the first longitudinal edge. Thus, the uniformity of the resulting compressed state of the body of the stent graft is further improved after inserting the rod into the hemstitch and threading the rod through the loops. If the loops are arranged on or in the area of the first longitudinal edge of the compression element, a further advantage of this measure is that the two longitudinal edges of the flap-shaped compression element can be connected directly to each other. Consequently, substantially the entire surface of the flap-shaped compression element is used to compress the body to its smallest possible diameter.

In another preferred embodiment, the hemstitch has several interruptions, wherein the loops are arranged in such a way that, in the longitudinal direction of the body, they are located at the level of the interruptions.

In this embodiment, the hemstitch has individual hemstitch portions between which one or more loops lie in each case when the rod is threaded through the hemstitch portions and the loops. The advantage of this measure is that, when the rod is pulled out of the loops and the hemstitch portions, the body of the stent graft is released successively in the longitudinal direction, in the manner of a zip fastener, and is expanded. In this way, the positioning of the stent graft in the blood vessel can be optimized in stages even during the gradual release of the stent graft. Moreover, the rod is visible in the areas of the interruptions of the hemstitch, as a result of which it is easy to detect an incorrect expansion procedure, i.e. when a portion of the body of the stent graft does not expand despite the rod being pulled out of the loops arranged on this portion of the body, and therefore countermeasures can be taken immediately.

In another preferred embodiment, the interruptions are at a uniform distance from one another.

This measure permits uniform fixing of the second longitudinal edge of the flap-shaped compression element.

In another preferred embodiment, the flap-shaped compression element is made of resorbable material.

The advantage of this measure is that, after the stent graft has been inserted and expanded, the compression element is able to degrade after it has performed its function. It will be appreciated that the material of the compression element is biocompatible. The compression element can also be made of a textile fabric, which may or may not be resorbable.

In another preferred embodiment, the flap-shaped compression element has a radial fold structure.

In the expanded state of the body, a stretching force of the stent graft, which causes the expansion, acts substantially on the surface spanned by the flap-shaped compression element, wherein the stent graft in the blood vessel is fixed more firmly in place by the radial fold structure. This measure advantageously increases the positional stability of the stent graft according to the invention in the expanded state.

In another preferred embodiment, the flap-shaped compression element has a low-friction, preferably formable, more preferably atraumatic surface.

The advantage of this measure is that the compression element can be inserted with minimal friction on the vessel wall and does not damage the vessel wall of the patient. Moreover, by virtue of its being formable, the sleeve catheter can easily conform to the inner shape or to the course of the blood vessel and bear snugly on the vessel wall.

In another preferred embodiment, the flap-shaped compression element is made of a textile material.

The advantage of this measure is that the compression element (flap) is substantially flexible compared to the sleeve catheter. It is thus possible to advance the stent graft system to the deployment site even in strongly tortuous vascular anatomies. Here, "textile material" is understood as any sheet-like textile structure, in particular ones composed of fibers, such as braids, wovens, meshes and knits. The fibers are endless fibers which are spinnable and which, as has been mentioned above, can be braided, woven, meshed or knitted.

Further advantages and features will become clear from the following description and from the attached drawing.

It will be appreciated that the aforementioned features and the features still to be explained below can be used not only in the respectively cited combination but also in other combinations or singly, without departing from the scope of the present invention.

BRIEF DESCRIPTION OF THE DRAWINGS

An illustrative embodiment of the invention is shown in the drawing and is described in more detail below with reference thereto. In the drawing:

FIG. 3 shows a side view of the stent graft from FIG. 1 in the compressed state;

FIG. 4 shows a detail of the stent graft from FIG. 3 in the compressed state, on a larger scale compared to FIG. 3;

FIG. 5 shows the stent graft in a state proceeding from the state in FIG. 3, at the start of its release;

FIG. 6 shows the stent graft in a further state during continued release;

DESCRIPTION OF PREFERRED EMBODIMENTS

Figure 1:
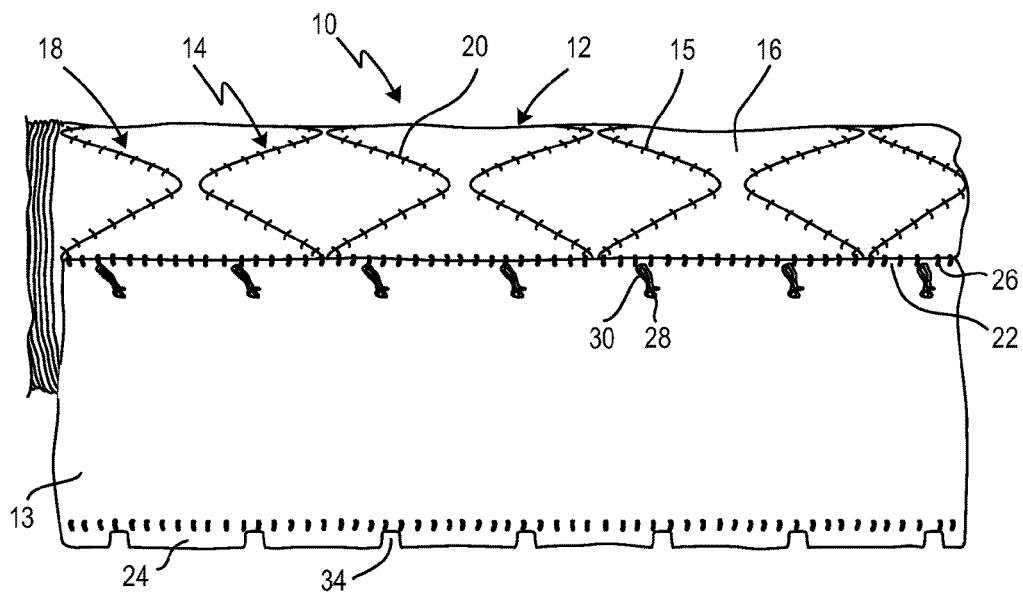
FIG. 1 shows a side view of a stent graft according to the invention in the fully expanded state.
Figure 2:
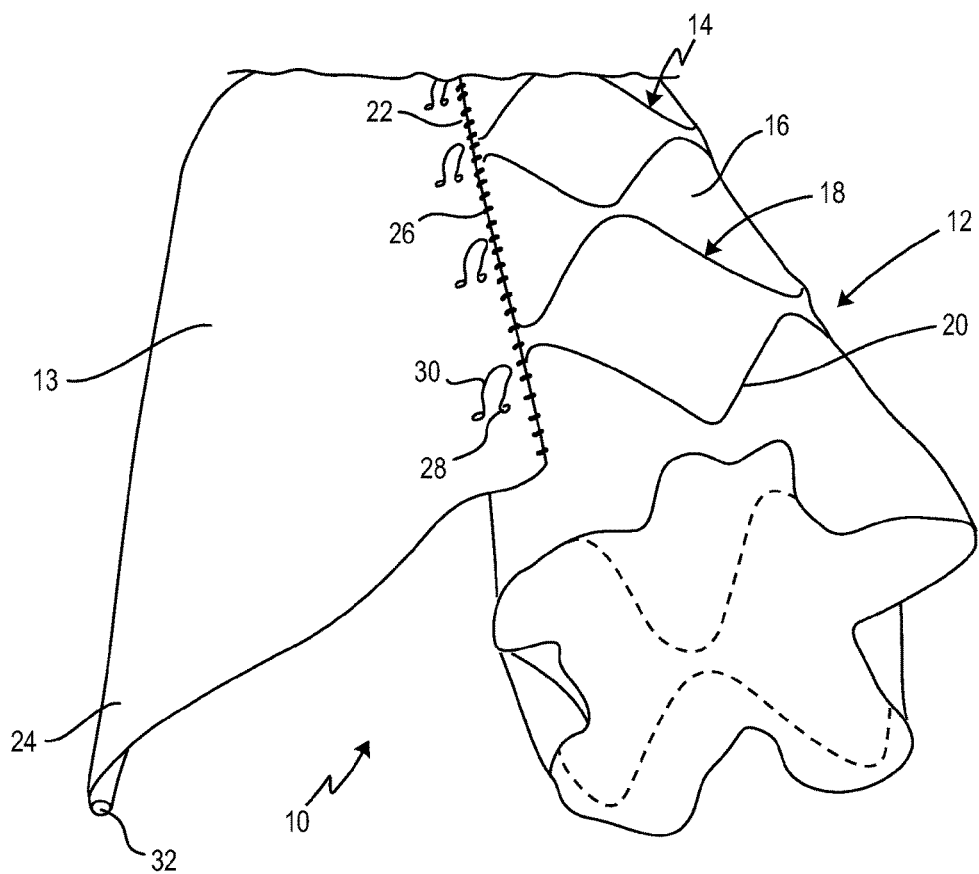
FIG. 2 shows a perspective view of part of the stent graft from FIG. 1 in the fully expanded state.

FIGS. 1 and 2 show an illustrative embodiment of a stent graft, designated generally by reference sign 10, which has a hollow cylindrical body 12 and a sleeve catheter, which is designed as a flap-shaped compression element 13. The body 12 has a self-expanding stent 14 and a prosthetic material 16. The stent 14 has ring segments 18 arranged in succession in the longitudinal direction of the hollow cylindrical body 12 and composed of meandering supports 20. The prosthetic material, for example a textile structure, is secured on the ring segments 18 by stitches 15, wherein the stitches are not shown in any of the subsequent figures.

As can be seen from the perspective view in FIG. 2, the body 12 is a hollow cylinder. The flap-shaped compression element 13 has a first longitudinal edge 22, secured on the body 12, and a free, second longitudinal edge 24, wherein the first longitudinal edge 22 is secured on the prosthetic material 16 by stitches 26. Perpendicularly with respect to both longitudinal edges 22, 24, the flap-shaped compression element 13 has an extent that corresponds substantially to the circumference of the body 12 in the compressed state. In the longitudinal direction, i.e. parallel to the longitudinal edges, the flap-shaped compression element 13 has substantially the same length as the body 12.

On the body 12 and/or the flap-shaped compression element 13, in this instance on the flap-shaped compression element 13, fixation points 28 are arranged which have loops 30 secured in the area of the first longitudinal edge 22 of the flap-shaped compression element 13. Moreover, on the second longitudinal edge 24, a hemstitch 32 is formed which has interruptions 34. The interruptions 34 of the hemstitch 32 are arranged in such a way that, in the longitudinal direction of the body 12, they are located at the level of the loops 30. Moreover, the interruptions 34 are spaced apart from one another by a uniform distance.

Before the stent graft 10 is inserted into a blood vessel (not shown) of a patient (not shown), the stent graft 10 is first of all compressed. The starting situation for the compression is shown in FIG. 1 and FIG. 2. Upon compression, the flap-shaped compression element 13 is placed around the body 12 in such a way that both longitudinal edges 22, 24 of the flap-shaped compression element 13 lie substantially one on the other. The body 12 is thus compressed radially to a circumference that is smaller than the circumference of the body 12 in the expanded state, as can be seen from FIG. 3 and FIG. 4.

In order to maintain the compressed state of the stent graft 10 before and during the insertion of the stent graft into a blood vessel, a rod 36 is introduced into the hemstitch 32 at a longitudinal end of the compression element 13 and is guided through the hemstitch 32. In this process, the loops 30, which are now located in the areas of the interruptions 34, are likewise threaded onto the rod 36. When, as is shown in FIG. 3, all of the loops 30 are threaded on the rod 36, the longitudinal edge 24 is fixed and the body 12 then retains the compressed state.

In this uniformly compressed state, the stent graft 10 can be inserted into a blood vessel of the patient and can be positioned at a site to be treated in the blood vessel. The body 12 is then released and brought to the expanded state by means of the rod 36 being pulled back out of the hemstitch 32 and the loops 30. The expansion of the body 12 then takes place automatically on account of the property of self-expansion of the stent 14.

In FIGS. 5 to 8, the stent graft 10 according to the invention is shown in several different stages during the successive release and expansion. To expand the stent graft 10, the rod 36 is gradually pulled out in the longitudinal direction from the hemstitch 32 and from the loops 32. As soon as a first of the loops 30 detaches from the rod 36, the longitudinal edge 24 of the flap-shaped compression element 13 comes loose at this point along a first portion 38 of the body 12, which first portion 38 is located between this first of the loops 30 and the next of the loops 30. On account of the self-expansibility of the stent 14, the first portion 38 of the body 12 stretches out into the expanded state. A further portion 40 of the body initially remains uniformly compressed. By means of the rod 36 being pulled further out, the remaining portions of the body 12 are gradually released and expanded.

In addition, it is possible to optimize the position of the stent graft 10 during the expansion of the body 12. In particular, the positioning of the stent graft 10 can be optimized in stages, by means of the rod 32 being pulled out of the hemstitch 32 in stages.

Figure 7:
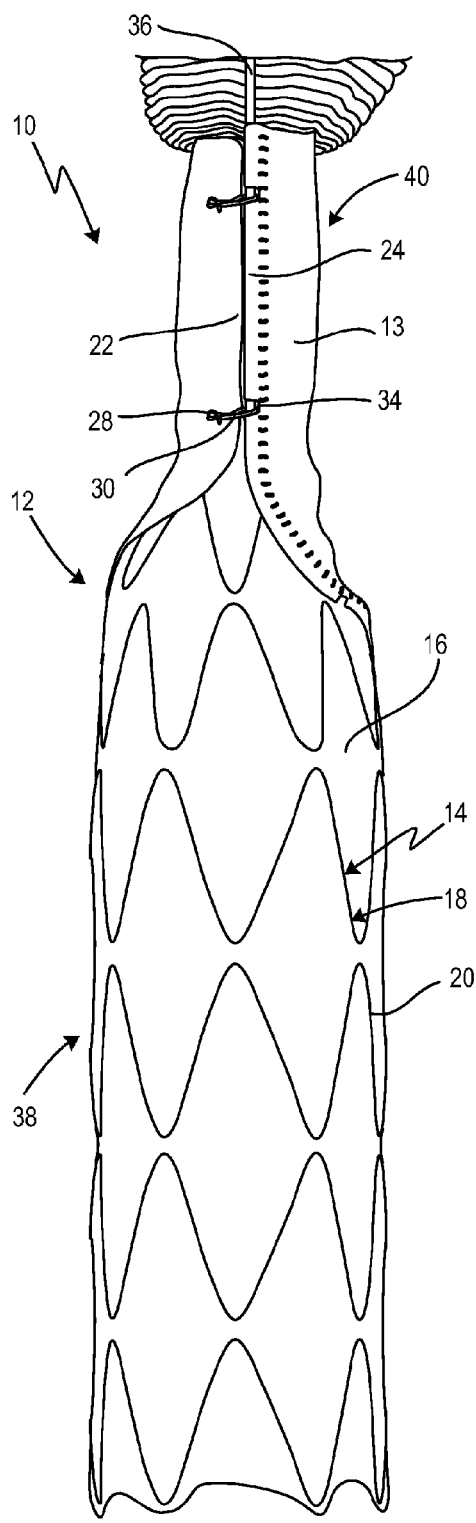
FIG. 7 shows the stent graft in a still further state upon further continuation of its release.

In one of the states of the stent graft 10 as shown in FIGS. 5 to 7, in which the stent graft 10 is still partially compressed and already partially expanded, in particular in a state as per FIGS. 5 and 6, the position of the stent graft 10 is able to be optimized by sliding and/or turning.

Figure 8:
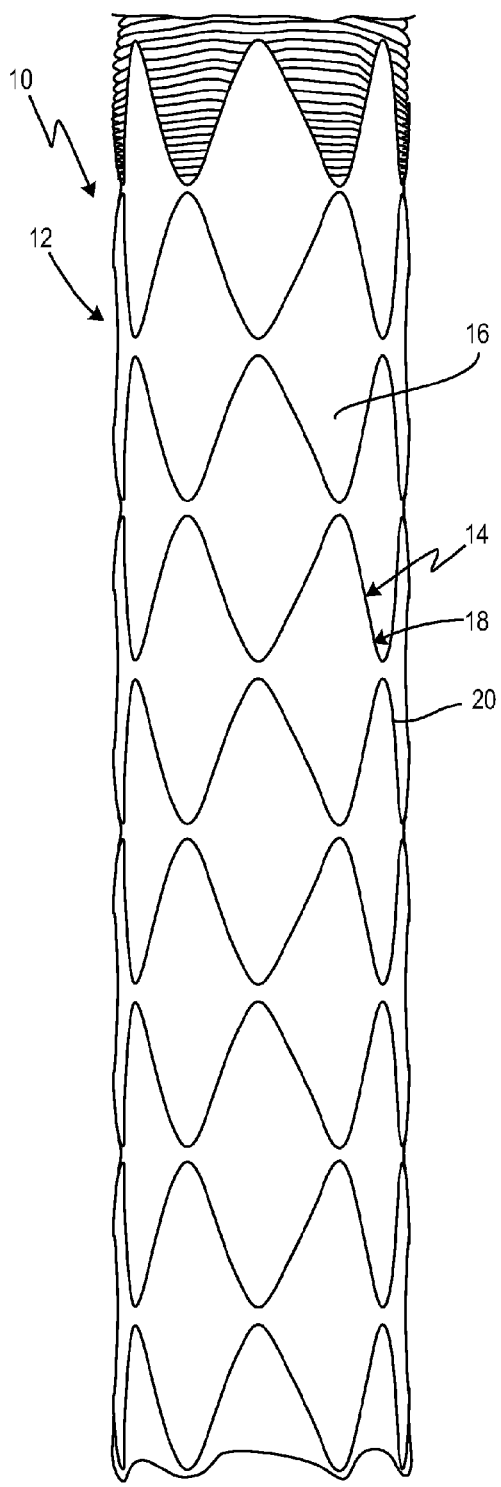
FIG. 8 shows the stent graft in the fully expanded state after complete release.

Once the positioning of the stent graft 10 has been optimized if appropriate, and no further corrections are to be made, the rod 36 can be pulled completely out of the hemstitch 32 in order to allow the stent graft 10 according to the invention to expand fully. The fully expanded state of the stent graft 10 is shown in FIG. 8. The compression element 13 (not visible in FIG. 8) remains on the body 12, i.e. it is still fixed with its first longitudinal edge 22 to the body 12.

The flap-shaped compression element 13 can be produced from textile fabric, it being possible for the shape, formability and surface nature of the flap-shaped compression element 13 to be adapted optimally to the requirements imposed by the shape and course of the blood vessels. In particular, the flap-shaped compression element 13 can have a radial fold structure which further increases the positional stability of the stent graft 10 according to the invention in the blood vessel. Using resorbable material, the flap-shaped compression element 13 can be produced such that it biodegrades after a certain period of time in the blood vessel. Irrespective of this, the compression element is preferably produced from a biocompatible material in order to ensure that treatment with the stent graft 10 according to the invention is as far as possible free of complications.

What is claimed is:

1. A stent graft comprising:
   a hollow cylindrical body and
   a sleeve catheter,
   wherein the body has at least one self-expanding stent and a prosthetic material, wherein the body, in a compressed state, has a circumference that is smaller than a circumference of the body in an expanded state,
   wherein the sleeve catheter is designed as a flap-shaped compression element having two longitudinal edges, a first longitudinal edge and a second longitudinal edge,
      wherein the first longitudinal edge is fixedly secured bar stitching the first longitudinal edge to the prosthetic material of the body,
      wherein an extent of the flap-shaped compression element perpendicular to the first longitudinal edge is smaller than the circumference of the body in the expanded state, wherein, for the purpose of compressing the body, the flap-shaped compression element can be placed around the body, and wherein the second longitudinal edge is not attached to the prosthesis material of the body and is releasably attachable to fixation points arranged on the flap-shaped compression element.

2. The stent graft as claimed in claim 1, wherein the flap-shaped compression element, in the compressed state of the body, extends perpendicularly with respect to the first longitudinal edge and at least fully circumferentially about the body.

3. The stent graft as claimed in claim 1, wherein the flap-shaped compression element has substantially the same length as the body.

4. The stent graft as claimed in claim 1, wherein the fixation points arranged on the flap-shaped compression element have loops through which a rod can be threaded for securing the second longitudinal edge of the flap-shaped compression element.

5. The stent graft as claimed in claim 4, wherein the second longitudinal edge of the flap-shaped compression element has a hemstitch into which the rod is insertable.

6. The stent graft as claimed in claim 5, wherein the hemstitch has several interruptions, wherein the loops are arranged in such a way that, in the longitudinal direction of the body, they are located at the level of the interruptions.

7. The stent graft as claimed in claim 6, wherein the interruptions are at a uniform distance from one another.

8. The stent graft as claimed in claim 1, wherein the flap-shaped compression element is made of textile fabric or resorbable material.

9. The stent graft as claimed in claim 1, wherein the flap-shaped compression element has a radial fold structure.

10. The stent graft as claimed in claim 1, wherein the flap-shaped compression element has a low-friction surface.

11. The stent graft as claimed in claim 1, wherein the flap-shaped compression element has a formable surface.

12. The stent graft as claimed in claim 1, wherein the flap-shaped compression element has an atraumatic surface.

* * * * *